(12) United States Patent
Kang et al.

(10) Patent No.: US 12,303,565 B2
(45) Date of Patent: May 20, 2025

(54) SELF-ASSEMBLED COMPLEX CONTAINING MAGNESIUM ION

(71) Applicant: Korea University Research and Business Foundation, Seoul (KR)

(72) Inventors: Heemin Kang, Seoul (KR); Gun Hyu Bae, Hwaseong-si (KR); Ramar Thangam, Gwangju-si (KR)

(73) Assignee: Korea University Research and Business Foundation, Seoul (KR)

( * ) Notice: Subject to any disclaimer, the term of this patent is extended or adjusted under 35 U.S.C. 154(b) by 135 days.

(21) Appl. No.: 17/234,081

(22) Filed: Apr. 19, 2021

(65) Prior Publication Data

US 2022/0111059 A1 Apr. 14, 2022

(30) Foreign Application Priority Data

Oct. 14, 2020 (KR) ........................ 10-2020-0132898

(51) Int. Cl.
*A61K 47/54* (2017.01)

(52) U.S. Cl.
CPC ................................. *A61K 47/549* (2017.08)

(58) Field of Classification Search
CPC ... A61K 47/549; A61K 47/52; A61K 31/7076
See application file for complete search history.

(56) References Cited

U.S. PATENT DOCUMENTS

| | | |
|---|---|---|
| 2016/0022707 A1 | 1/2016 | Zhong et al. |
| 2018/0169141 A1 | 6/2018 | Bian et al. |

FOREIGN PATENT DOCUMENTS

| | | |
|---|---|---|
| CN | 111317826 B | 6/2020 |
| JP | 2009-512728 A | 3/2009 |

OTHER PUBLICATIONS

Hammes et al., Biochemistry, 1964, 3(10), p. 1504-1506. (Year: 1964).*
Swainston et al., Metabolomics, 2016, 12, 109, 7 pages. (Year: 2016).*
Polimeni et al., Circulation Research, 1973, 33(4), p. 367-374. (Year: 1973).*
Gjevre et al., Comp. Biochem. Physiol., 1996, 115A(2), p. 159-168. (Year: 1996).*
Definition of encapsulate, Oxford English Dictionary, https://www.oed.com/, accessed online on Apr. 25, 2023. (Year: 2023).*
Meksuriyen et al., Journal of Biological Chemistry, 1998, 273(47), p. 30939-30944. (Year: 1998).*
Frankel et al., Langmuir, 2016, 32, p. 2041-2049. (Year: 2016).*
Definition of "coagulate", Oxford English Dictionary, www.oed.com, accessed online on Oct. 17, 2023. (Year: 2023).*
EPO English machine translation of CN 111317826 A, https://worldwide.espacenet.com/, accessed online on Oct. 17, 2023 (Year: 2023).*
Van Wazer et al., Chemical Reviews, 1958, 58(6), p. 1011-1046. (Year: 1958).*
Liang et al., Chem. Commun., 2015, 51, p. 15196-15199. (Year: 2015).*
Office Action issued May 31, 2022 in Japanese Application No. 2021-074175.
Ting Zhang et al., "Self-Assembly of DNA-Minocycline Complexes by Metal Ions with Controlled Drug Release", ACS Applied Materials & Interfaces, 2019, vol. 11, pp. 29512-29521 (10 pages total).
N.G. Holm, "The significance of Mg in prebiotic geochemistry", Geobiology, 2012, vol. 10, pp. 269-279 (11 pages total).

* cited by examiner

*Primary Examiner* — Jonathan S Lau
(74) *Attorney, Agent, or Firm* — Sughrue Mion, PLLC (57) ABSTRACT

The present invention relates to an effective component delivery system using self-assembly and self-disassembly of a self-assembled complex, and the effective component delivery system uses a self-assembled complex which is composed of substances existing in the body, thereby being less toxic and harmless to the human body, and the effective component delivery system is capable of controlling a self-disassembly rate and an effective component release rate by using various kinds of metal ions and ligands including phosphate or phosphonate.

18 Claims, 6 Drawing Sheets

SELF-ASSEMBLED COMPLEX CONTAINING MAGNESIUM ION

CROSS-REFERENCE TO RELATED APPLICATION

This application claims priority to and the benefit of Korean Patent Application No. 10-2020-00132898, filed on Oct. 14, 2020, the disclosure of which is incorporated herein by reference in its entirety.

TECHNICAL FIELD

The present invention relates to a self-assembled complex capable of performing reversible self-assembly and self-disassembly, and particularly, to a self-assembled complex in which ligands including phosphate or phosphonate and metal ions based on substances existing in the body are self-assembled, and various effective components are contained, and which is capable of controlling a rate of self-disassembly by using metal ions and ligands, and an effective component delivery system which delivers effective components by using the characteristics of the self-assembly and the self-disassembly of the self-assembled complex.

BACKGROUND ART

A Drug Delivery System (DDS) may be defined as a formulation to effectively deliver minimum drug amounts required for disease treatment by minimizing the side effects of existing drugs and optimizing the efficacy and the effects of drugs.

The DDS field is recognized as the core of the next-generation bio industry by enabling the development of new formulations of existing drugs with low cost and short development period. In the field of the DDS, research to develop new drug delivery agents by using biopolymers and synthetic polymers exhibiting various functions and performance is being actively conducted.

The existing drug delivery agent uses a self-assembled complex using bisphosphonate that does not exist inside the human body and metal ions.

The existing DDS has toxicity problems because carriers, such as nanoparticles using the substances that do not exist in the body are used, price competitiveness is not guaranteed due to the delivery of growth factors, proteins, and the like, and there is a problem that the sustained drug release is not controlled, so that the drug release is limited to a short period of time.

Accordingly, there is a need to develop a drug delivery system capable of controlling sustained release of drugs or molecules, and effective components while being less toxic and harmless than existing technology by using substances existing in the body.

PRIOR ART LITERATURE

Patent Document (Patent Document 1) US Patent Application Publication No. US2018169141 (published on Jun. 21, 2018)

SUMMARY OF THE INVENTION

The present invention is conceived to solve the foregoing problems and is to provide a self-assembled complex which is capable of continuously delivering effective components by controlling a rate of self-disassembly of the self-assembled complex containing various effective components based on substances existing in the body, and including metal ions and ligands, and an effective component delivery system using the same.

In order to solve the technical problem, the present invention provides a self-assembled complex and a system for delivering effective components using the same.

An exemplary embodiment of the present invention provides a self-assembled complex composed of substances existing in a body, the self-assembled complex including: one or more metal ions and ligands that are ion-bonded with the metal ion, in which the self-assembled complex is reversibly self-assembled or self-disassembled, and the self-assembly is performed by any one or more of the concentration of the metal ion and the concentration of the ligand, a self-disassembly rate is controlled by the kind of ligand, and any one or more of the metal ion, the ligands, and effective components are continuously released during a first release time.

The self-assembled complex according to the present invention is composed of substances existing in the body, thereby being less toxic and harmless to the human body, and is capable of controlling a self-disassembly rate and an effective component release rate by using ligands including phosphate or phosphonate.

DETAILED DESCRIPTION

Hereinafter, in order to describe the present invention more specifically, an exemplary embodiment of the present invention will be described in more details with reference to the accompanying drawings. However, the present invention is not limited to the exemplary embodiment described herein and may also be specified in other forms.

The present invention provides a self-assembled complex composed of substances existing in the body, the self-assembled complex including: one or more metal ions and ligands which are ion-bonded with the metal ion, in which the self-assembled complex is reversibly self-assembled or self-disassembled and is self-assembled by a concentration of any one or more of the metal ion and the ligand, a self-disassembly rate is controlled by the kind of ligand, and one or more of the metal ions, the ligands, and effective components are continuously released for a first release time.

Figure 1:
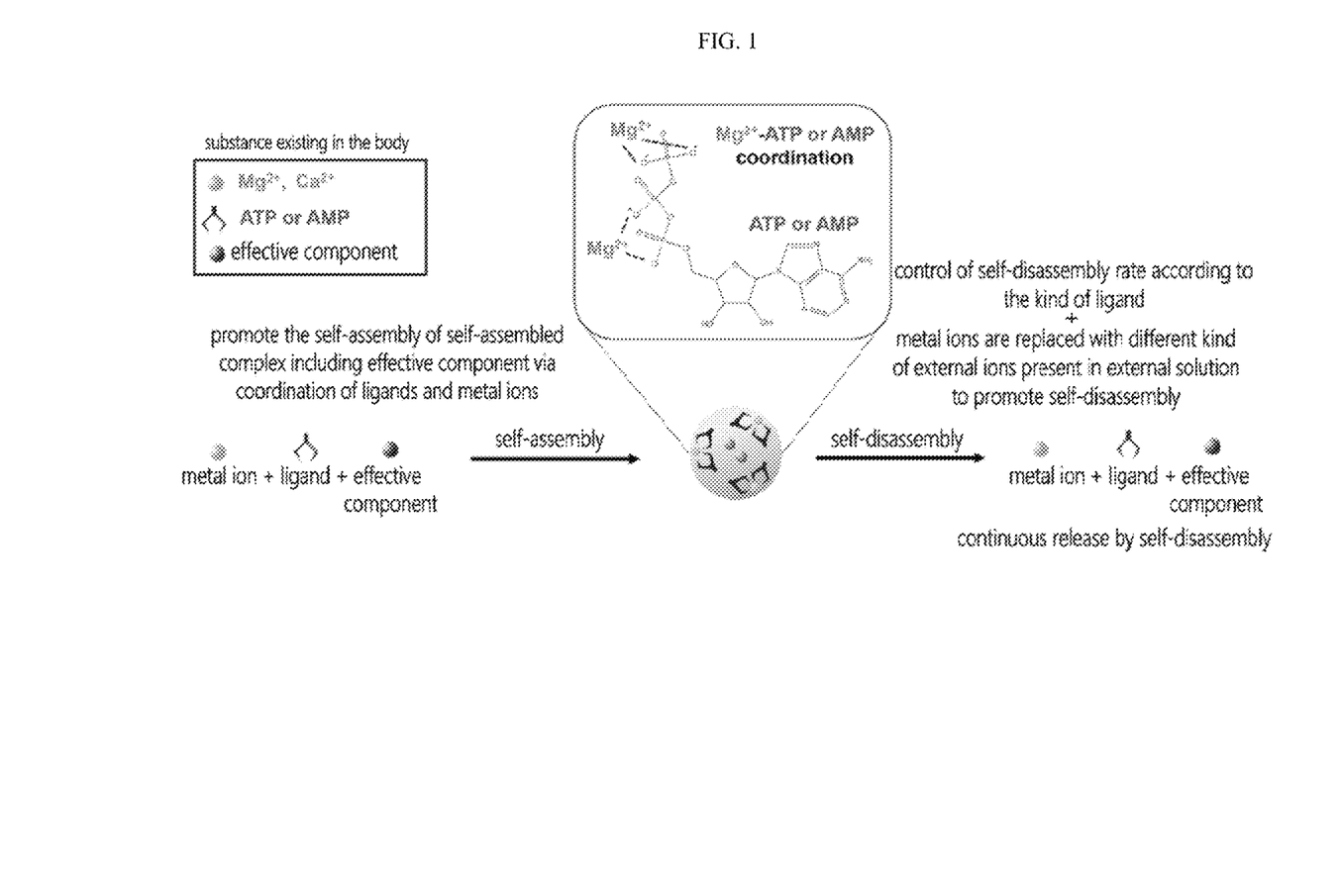
FIG. 1 is a schematic diagram illustrating a self-assembly and self-disassembly mechanism of a self-assembled complex according to an exemplary embodiment of the present invention.

FIG. 1 is a schematic diagram illustrating a self-assembly and self-disassembly mechanism of a self-assembled complex according to an exemplary embodiment of the present invention. Referring to FIG. 1, a self-assembled complex of the present invention has the form in which one or more ligands and one or more metal ions are ion-bonded and may further contain one or more effective components. Further, the metal ion existing in the self-assembled complex of the present invention is self-disassembled while being exchanged to external ion present in an external solution, so that the self-assembled complex may continuously release the metal ion and the effective components for a long time.

The self-assembled complex further includes one or more effective components, a self-disassembly rate is controlled by the kind of ligand, and the one or more effective components may be continuously released for the first release time.

In the present specification, the "substances existing in the body" means substances composed of constituent components existing in the body, not an artificially synthesized substance.

In particular, in the self-assembled complex according to the present invention, one or more metal ions, one or more ligands, and one or more effective components may be included and coagulated. More particularly, the self-assembled complex has the form in which one or more effective components are included in one self-assembled complex and coagulated.

More particularly, an average size of the self-assembled complex of the present invention may be 0.2 to 5 µm, 0.5 to 3 µm, or 0.5 to 2 µm. The self-assembled complex has the foregoing size, so that it is advantageous for self-assembly and may release the substance existing in the complex for a long time.

For example, the self-assembled complex of the present invention is self-disassembled to continuously release any one or more of the metal ions and the effective components for 20 days or more, 25 days or more, or 28 days or more.

The self-assembled complex of the present invention is self-assembled by any one or more of a concentration of the metal ions and a concentration of ligands, and a self-disassembly rate may be controlled by the kind of external ion. The self-assembled complex may include adenosine.

In particular, when the concentration of the metal ions is 1 to 30 mM, 1 to 25 mM, or 10 to 25 mM, two or more of the metal ions, the ligands, and the effective components are self-assembled to form the self-assembled complex. In particular, the metal ion and the ligand may be self-assembled, or the metal ion, the ligand, and the effective components are self-assembled to form the self-assembled complex.

Further, when the concentration of ligand is 10 to 70 mM, 20 to 60 mM, or 25 to 55 mM, two or more of the metal ions, the ligands, and the effective components are self-assembled to form the self-assembled complex. In particular, the metal ion and the ligand may be self-assembled, or the metal ion, the ligand, and the effective components are self-assembled to form the self-assembled complex.

The metal ion may include any one or more of calcium, magnesium, strontium, barium, manganese, iron, cobalt, and nickel ions. In particular, the metal ions may include calcium or magnesium ions. The self-assembled complex includes the metal ions and is absorbed into the body, thereby improving a biological function and being harmless to the human body.

The external ion included in the external solution may include ions of any one or more of calcium, sodium, potassium, phosphate, hydrogen, and hydroxide. The metal ions in the self-assembled complex may be released by using the external ions. The hydrogen ions or hydroxide ions contained in the external solution may facilitate the self-disassembly of the self-assembled complex, and the different kind of external ions present in the solution are essential conditions, but in the case of acidic or basic conditions during the self-disassembly, the hydrogen ions or the hydroxide ions may further facilitate the self-disassembly.

In particular, the self-assembled complex of the present invention is self-disassembled by the external solution including the external ion, but the amount of metal ions released may be controlled by the kind of external ion.

For example, the amount of metal ions released in the case where the external ion is the ion of calcium, hydrogen, or hydroxide may be 1.5 times to 3 times, 1.5 times to 2 times, or 2 times to 3 times of the amount of metal ions released in the case where the external ion is the ion of sodium, potassium, or phosphate.

The ligand may include any one or more of phosphate and phosphonate, and in particular, the ligand may include any one or more of adenosine monophosphate, adenosine diphosphate, adenosine triphosphate, and 2-aminoethylphosphonic acid. In particular, the ligand may be adenosine monophosphate, adenosine diphosphate, adenosine triphosphate, or 2-aminoethylphosphonic acid. The self-assembled complex includes the ligand so that it is possible to gradually release the metal ions by the external ions, and a self-disassembly rate of the self-assembled complex may be controlled according to the kind of ligand. The self-assembled complex may include a plurality of ligands, and when the self-assembled complex includes the plurality of ligands, the bonding form with the metal ions is different according to the kind of ligand, so that the self-disassembly rate of the self-assembled complex may be proportionally exhibited according to a mixing ratio of the plurality of ligands.

The self-disassembly rate in the case where the ligand includes one phosphate may be faster than the self-disassembly rate in the case where the ligand includes two or more phosphates by 2 times to 6 times, 2 times to 4 times, or 3 times to 5 times.

The effective components may include a one or more of any kind of drug, small molecules, polymers, and proteins, and in particular, the effective component may include any one or more of adenosine, guanosine, uridine, cytidine, and dexamethasone. The effective component is a substance to be delivered to the body, is released during the self-disassembly of the self-assembled complex, and is supplied to the body.

Further, the present invention provides an effective component delivery system using the self-assembled complex.

The effective component delivery system according to the present invention includes a self-assembled complex based on substances existing in the body and is less toxic than a technology using existing synthetic polymers, thereby delivering substances in a state that is harmless to the human body.

The effective components may include any one or more of drugs, small molecules, polymers, and proteins, and in particular, the effective component may include any one or more of adenosine, guanosine, uridine, cytidine, and dexamethasone.

In particular, referring to FIG. 1, the self-assembled complex according to the present invention controls a self-disassembly rate according to the kind of ligand, and the metal ion of the self-assembled complex is replaced with the external ion present in the external solution to promote self-disassembly. The self-assembly is performed according to the concentration of the metal ions and the concentration of ligands existing in the self-assembled complex and the external ion present in the external solution may control the amount of metal ions released during the self-disassembly and a self-disassembly rate of the self-assembled complex is controlled according to the kind of ligand and the kind of external ion.

In the effective component delivery system of the present invention, the metal ion existing in the self-assembled complex is released as it is replaced with the external ion present in the external solution, and the release of the ligand and the effective component is promoted as the metal ion of the self-assembled complex is released. In particular, the amount of metal ions released from the self-assembled complex may be controlled according to the kind of external ion present in the external solution.

In particular, the amount of metal ions released in the case where the external ion is the ion of calcium, hydrogen, or hydroxide may be 1.5 times to 3 times, 1.5 times to 2 time, or 2 times to 3 times of the amount of metal ions released in the case where the external ion is the ion of sodium, potassium, and phosphate.

Further, the bonding form with the metal ion is different according to the kind of ligand of the self-assembled complex of the present invention, thereby controlling the self-disassembly rate of the self-assembled complex and the release rate of the effective components.

The self-disassembly rate in the case where the ligand includes one phosphate may be faster than the self-disassembly rate in the case where the ligand includes two or more phosphates by 2 times to 6 times, 2 times to 4 times, or 3 times to 5 times.

Hereinafter, examples of the present invention will be described. However, the examples below are merely preferable examples of the present invention, and the scope of the present invention is not limited by the examples.

1. Prepare Self-Assembled Complex

Example 1 (Mg-ATP-Adenosine)

In order to prepare Mg-ATP-adenosine self-assembled complex, a solution of adenosine triphosphate (ATP) 25 mmol/L (27.6 mg ATP in 2 mL DI water), magnesium chloride heptahydrate ($MgCl_2$-$7H_2O$) 25 mmol/L (10.1 mg $Mg^{2+}$ in 2 mL DI water) and adenosine 25 mmol/L (13.4 mg adenosine in 2 mL DI water) were mixed to form the adenosine self-assembled complex. Briefly, the ATP (2 mL) was mixed with magnesium chloride heptahydrate ($MgCl_2$-$7H_2O$) solution in a 4:5 ratio at room temperature (25° C.) for 30 seconds to form a mixture. The mixture was further treated with an adenosine solution by a drop by drop manner to form the Mg-ATP-adenosine self-assembled complex.

Example 2 (Mg-AMP-Adenosine)

In order to prepare Mg-AMP-adenosine self-assembled complex, a solution of adenosine monophosphate (AMP) 10 mmol/L (6.9 mg AMP in 2 mL DI water), magnesium chloride heptahydrate ($MgCl_2$-$7H_2O$) 10 mmol/L (4 mg $Mg^{2+}$ in 2 mL DI water) and adenosine 50 mmol/L (26.7 mg adenosine in 2 mL DI water) were mixed to form an adenosine self-assembled complex. Briefly, the AMP (2 mL) was mixed with the magnesium chloride heptahydrate solution in a 4:5 ratio at room temperature (25° C.) for 30 seconds to form a mixture. The mixture was further treated with an adenosine solution by a drop by drop manner to form the Mg-AMP-adenosine self-assembled complex.

Experimental Example

In order to observe the self-assembled complex according to the present invention, 500 uL each of the self-assembled complexes of Mg-ATP and Mg-AMP prepared in Examples 1 and 2 was mixed with adenosine solutions, and the mixtures were prepared on glass substrates having a size of 22×22 mm in a 6-well plate and washed repeatedly with deionized water. After 30 minutes, the washed solutions were treated with hydrochloric acid (HCl) and dried for 24 hours in an oven at 37° C. Before the preparation of the self-assembled complex, the hydroxyl group on the substrate was activated by immersing the glass substrate in sulfuric acid ($H_2SO_4$) for 1 hour and then washed with DI water. The glass substrate was immersed in a mixed solution in which HCl and methanol are mixed in a ratio of 1:1 and washed with DI water. The activated glass substrate was thiolated by incubation in methanol containing 0.5 mM mercaptosilatrane for 1 hour under a dark condition and then washed with methanol. The self-assembled complex was observed by using a Scanning Electron Microscope (SEM) in order to check the form of the prepared self-assembled complex.

The prepared glass substrates were fixed in a 6-well plate and 1×PBS solution and 2 mL of calcium chloride solution (100 mmol/L) were added to the cover glass in all the wells. Then, the glass substrates were positioned well so as not to float on the added solution and the plates were sealed with parafilm, coated, and stored in an incubator at 37° C.

Furthermore, the sample solutions (200 µL) were collected from the wells of 1 to 6 at the $1^{st}$, $3^{rd}$, $7^{th}$, $14^{th}$, $21^{st}$, and $28^{th}$ days for the release analysis, and the external solution was filled up as much as the extracted amount.

The collected solutions were stored in the 1.5 mL microtube at 4° C. The concentration of released magnesium ($Mg^{2+}$), ATP/AMP, and adenosine (effective components) was measured by spectrometry after all solutions are extracted until $1^{st}$, $3^{rd}$, $7^{th}$, $14^{th}$, $21^{st}$, and $28^{th}$ day.

Further, colorimetric assay kit (Biovision) protocol was followed in order to assess the release of magnesium ($Mg^{2+}$) and measure the change in an adenosine (effective component) concentration over the time of release.

Similarly, for the assessment of adenosine release, the adenosine assay kit (abcam) was used to measure the change in the adenosine concentration over time.

By using multi-well microplate reader, the absorption of magnesium ($Mg^{2+}$) at 603 and 450 nm wavelength was measured by using Hidex's sense model, and for adenosine, Ex/Em=535/575 nm was used to measure the fluorescence.

After 28 days, the glass substrate was completely dried at 37° C. for 24 hours and was observed by using the SEM.

Figure 2:
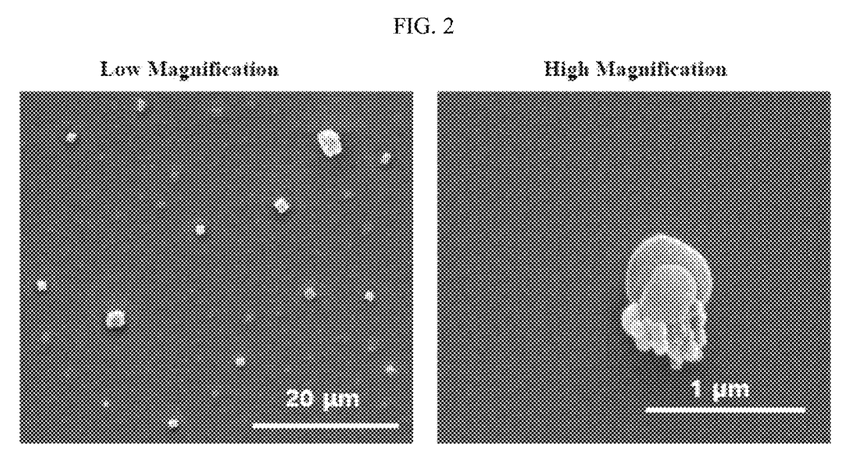
FIGS. 2 and 3 are Scanning Electron Microscope (SEM) images of the self-assembled complex according to the exemplary embodiment of the present invention.
Figure 3:
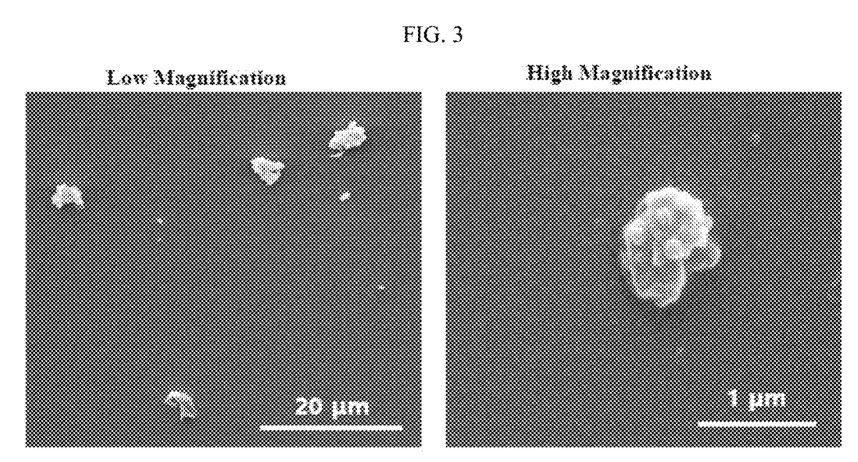

FIGS. 2 and 3 are SEM images of the self-assembled complex according to the exemplary embodiment of the present invention. FIG. 2 is an image of the self-assembled complex of Example 1 and FIG. 3 is an image of the self-assembled complex of Example 2. Referring to FIGS. 2 and 3, it can be seen that the self-assembled complex is formed with a size of 0.5 to 1 µm.

Figure 4:
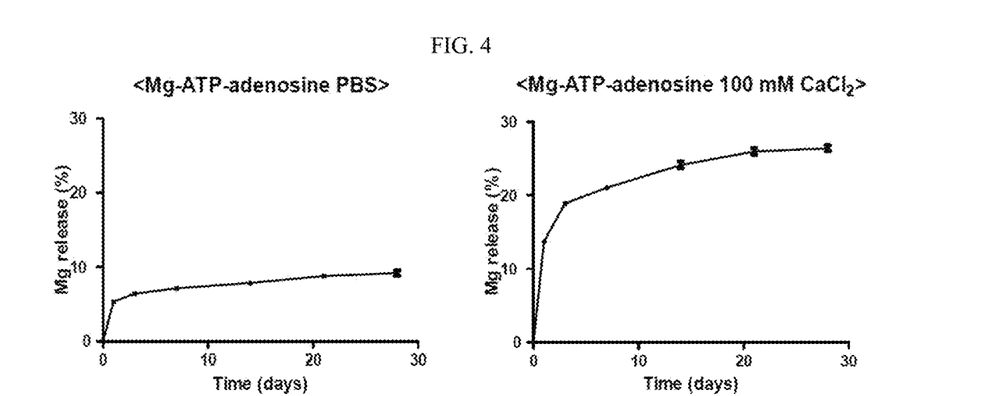
FIGS. 4 and 5 are graphs representing the amount of accumulated magnesium released from the self-assembled complex over time for each solution having a different kind and concentration of external ions according to the exemplary embodiment of the present invention.
Figure 5:
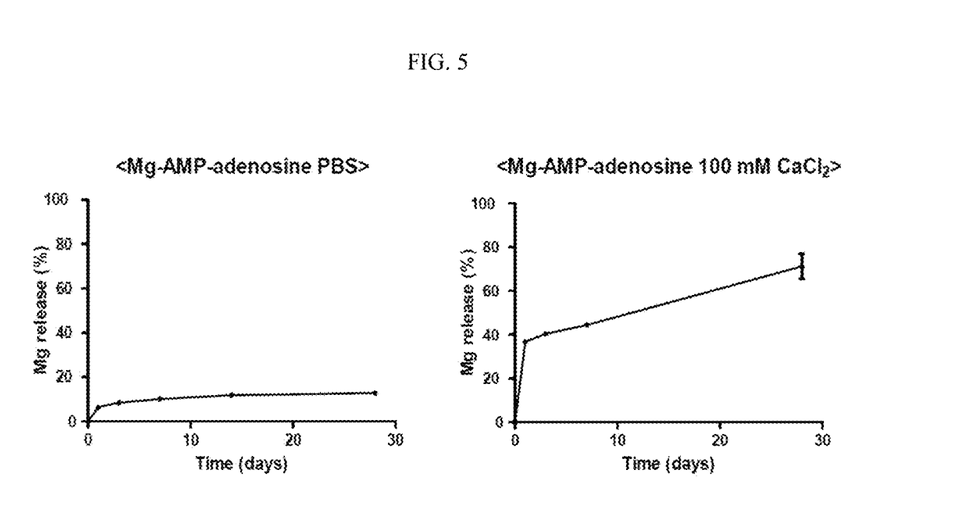

FIGS. 4 and 5 are graphs representing the amount of accumulated magnesium released from the self-assembled complex over time for each solution having a different kind and concentration of external ions according to the exemplary embodiment of the present invention. FIG. 4 is a graph representing the amount of accumulated magnesium released over time for each external solution of the self-assembled complex of Example 1, and FIG. 5 is a graph representing the amount of accumulated magnesium released over time for each external solution of the self-assembled complex of Example 2. Referring to FIGS. 4 and 5, the amounts of magnesium released from the self-assembled complexes incubated in the PBS external solution and the calcium chloride external solution were measured and it can be seen that magnesium was continuously released for 28 days in both the self-assembled complexes of Examples 1 and 2. Further, it can be seen that compared to the PBS external solution, the larger amount of magnesium was released in the calcium chloride external solution. From this, it can be seen that calcium ions are provided from calcium chloride so that magnesium ions are released. Further, it can be seen that the amount of magnesium released of the self-assembled complex including the AMP is larger than that of the self-assembled complex including the ATP.

Through this, it can be seen that the release of the magnesium ion from the self-assembled complex is required during the drug delivery. Further, the released magnesium ion is the important factor to tissues so that the magnesium ion is harmless to the body. Furthermore, the rapid absorption of the magnesium ion in the region, to which the magnesium ion is delivered, may further increase the biological function.

Figure 6:
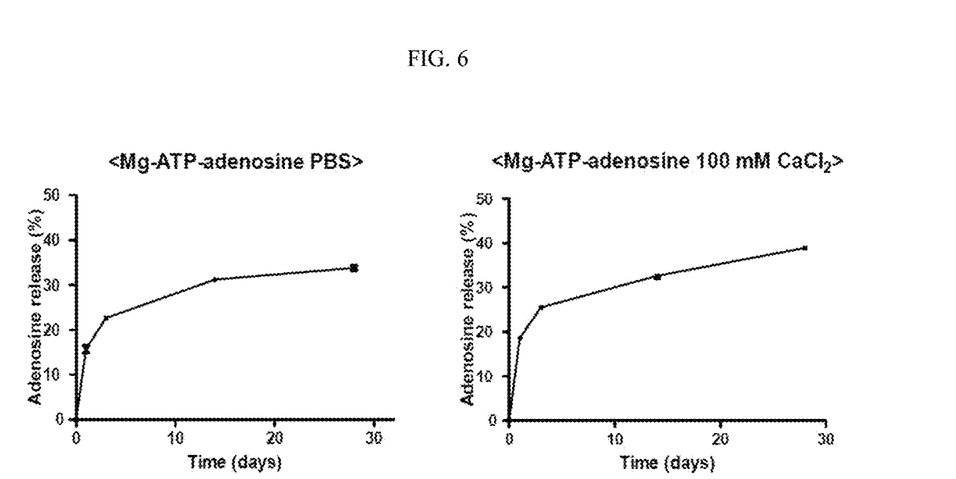
FIGS. 6 and 7 are graphs representing the amount of accumulated adenosine released from the self-assembled complex over time for each solution having a different kind and concentration of external ions according to the exemplary embodiment of the present invention.
Figure 7:
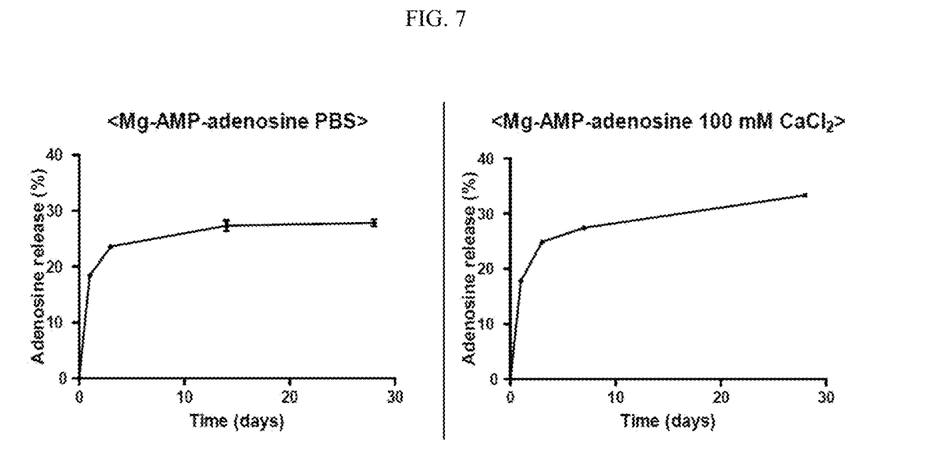

FIGS. 6 and 7 are graphs representing the amount of accumulated adenosine released from the self-assembled complex over time for each solution having a different kind and concentration of external ions of the self-assembled complex according to the exemplary embodiment of the present invention. FIG. 6 is a graph representing the amount of accumulated adenosine released over time for each external solution of the self-assembled complex of Example 1, and FIG. 7 is a graph representing the amount of accumulated adenosine released over time for each external solution of the self-assembled complex of Example 2.

Referring to FIGS. 6 and 7, the amounts of adenosine that is the effective component released from the self-assembled complex incubated in the PBS external solution and the calcium chloride external solution were measured, and it can be seen that adenosine that is the effective component was continuously released for 28 days from both the self-assembled complexes of Examples 1 and 2. The minimum release of the adenosine under PBS was observed, which represents an increase in loss of the magnesium ion. In contrast to this, the faster release of magnesium ion and adenosine from the self-assembled complexes under the calcium chloride may be due to the ion-stabilizing mechanisms lacking, which were found in the complexes. In addition, the adenosine regulates the significant impact on calcium-dependent bone metabolism by modulating osteogenic differentiation. Considering these possible merits of adenosine, the magnesium-associated ATP/AMP dependent self-assembled complex serves as a functional carrier in a biomedical application field.

Figure 8:
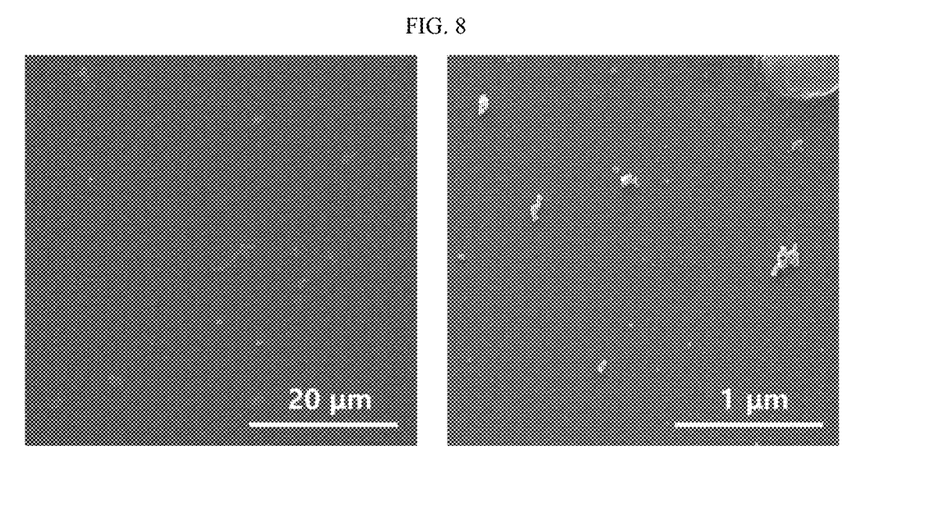
FIGS. 8 and 9 are Scanning Electron Microscope (SEM) images after 28 days of the drug release of the self-assembled complex according to the exemplary embodiment of the present invention.
Figure 9:
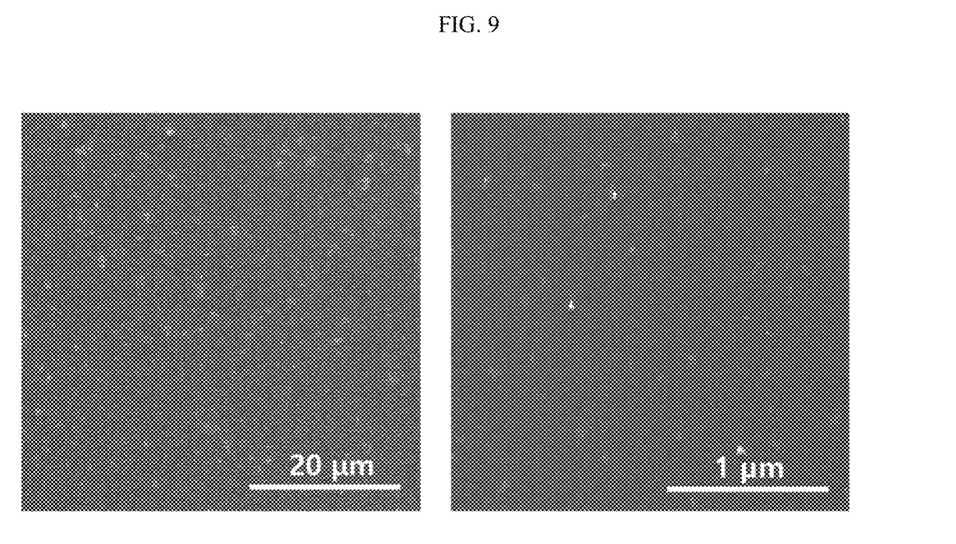

FIGS. 8 and 9 are SEM images after 28 days of the drug release of the self-assembled complex according to the exemplary embodiment of the present invention. FIG. 8 is an image of the self-assembled complex of Example 1 and FIG. 9 is an image of the self-assembled complex of Example 2.

Referring to FIGS. 8 and 9, the dissociation levels of the complexes could be checked through the scanning electron microscopy after the complete release of the self-assembled complex on 28th day. This shows the potential release of the self-assembled complexes in sustained gradual release of Mg' with ATP or AMP and adenosine. Moreover, the increased release of local concentration of calcium ions as well as both magnesium ions and calcium ions may further facilitate the release of adenosine with ATP/AMP from the self-assembled complex to induce natural molecular delivery approaches, and the self-assembled complex is non-toxic with safe materials for biomedical applications to further promote physical and biological functionalities.

In conclusion, the self-assembled complex according to the present invention is stable and exhibits a well-defined structure under the release, and is a powerful tool for the synthesis of functional natural molecular delivery systems for potential biomedical applications.

What is claimed is:

1. A self-assembled complex, comprising:
   one or more metal ions and ligands that are ion-bonded with the metal ion, the one or more metal ions and the ligands being coagulated, and
   one or more effective components contained by the one or more metal ions and ligands,
   wherein the one or more effective components is any one or more of adenosine,
   guanosine, uridine, cytidine, and dexamethasone,
   wherein the metal ions include ions of any one or more of magnesium, strontium, cobalt, and nickel.

2. The self-assembled complex of claim 1, wherein the first release time is 20 days or more.

3. The self-assembled complex of claim 1, wherein the ligand includes any one or more of phosphate and phosphonate.

4. The self-assembled complex of claim 3, wherein the ligand includes any one or more of adenosine monophosphate, adenosine diphosphate, adenosine triphosphate, and 2-aminoethylphosphonic acid.

5. The self-assembled complex of claim 1, wherein the self-disassembly rate in the case where the ligand includes one phosphate is controlled 2 to 6 times faster than the self-disassembly rate in the case where the ligand includes two or more phosphate.

6. The self-assembled complex of claim 1, wherein the self-assembled complex is self-assembled in the case where a concentration of the metal ions is 1 to 30 mM.

7. The self-assembled complex of claim 1, wherein the self-assembled complex is self-assembled in the case where a concentration of the ligands is 10 to 70 mM.

8. An effective component delivery system comprising the self-assembled complex according to claim 1.

9. The self-assembled complex of claim 1, wherein the metal ions include ions of strontium.

10. The self-assembled complex of claim 1, wherein the metal ions include ions of cobalt.

11. The self-assembled complex of claim 1, wherein the metal ions include ions of nickel.

12. The self-assembled complex of claim 1, wherein the effective component is adenosine.

13. The self-assembled complex of claim 1, wherein the effective component is guanosine.

14. The self-assembled complex of claim 1, wherein the effective component is uridine.

15. The self-assembled complex of claim 1, wherein the effective component is cytidine.

16. The self-assembled complex of claim 1, wherein the effective component is dexamethasone.

17. The self-assembled complex of claim 1, wherein the effective component is adenosine and the ligand is adenosine triphosphate.

18. The self-assembled complex of claim 1, wherein the effective component is adenosine and the ligand is adenosine monophosphate.

\* \* \* \* \*